(12) United States Patent
Panotopoulos

(10) Patent No.: US 9,623,177 B2
(45) Date of Patent: Apr. 18, 2017

(54) FLUID EXCHANGE CATHETER SYSTEM

(71) Applicant: IRRAS AB, Stockholm (SE)

(72) Inventor: Christos Panotopoulos, Athens (GR)

(73) Assignee: IRRAS AB, Stockholm (SE)

( * ) Notice: Subject to any disclaimer, the term of this patent is extended or adjusted under 35 U.S.C. 154(b) by 949 days.

(21) Appl. No.: 13/769,524

(22) Filed: Feb. 18, 2013

(65) Prior Publication Data

US 2013/0158470 A1 Jun. 20, 2013

Related U.S. Application Data

(62) Division of application No. 12/065,019, filed as application No. PCT/GR2006/000043 on Aug. 25, 2006, now Pat. No. 8,398,581.

(30) Foreign Application Priority Data

Sep. 2, 2005 (GR) .............................. 20050100452

(51) Int. Cl.
*A61M 5/168* (2006.01)
*A61M 1/00* (2006.01)
*A61M 25/00* (2006.01)

(52) U.S. Cl.
CPC ...... *A61M 5/16804* (2013.01); *A61M 1/0062* (2013.01); *A61M 1/0064* (2013.01); *A61M 25/007* (2013.01); *A61M 25/0021* (2013.01); *A61M 1/0058* (2013.01); *A61M 1/0084* (2013.01); *A61M 2025/0039* (2013.01)

(58) Field of Classification Search
CPC .................. A61M 5/16804; A61M 2025/0039
See application file for complete search history.

(56) References Cited

U.S. PATENT DOCUMENTS

| 2,560,915 | A |   | 7/1951 | Bamberger |
| 3,189,031 | A | * | 6/1965 | Andersen .......... A61M 25/0069 |
|   |   |   |   | 604/270 |
| 3,669,116 | A |   | 6/1972 | Heyer |
| 3,812,855 | A | * | 5/1974 | Banko ................ A61F 9/00736 |
|   |   |   |   | 137/205 |
| 3,955,574 | A |   | 5/1976 | Rubinstein |

(Continued)

FOREIGN PATENT DOCUMENTS

| EP | 0251512 A1 | 1/1988 |
| GB | 1451418 A | 10/1976 |

(Continued)

*Primary Examiner* — Laura Bouchelle
*Assistant Examiner* — Anh Bui
(74) *Attorney, Agent, or Firm* — The Webb Law Firm

(57) ABSTRACT

A method of infusing and aspirating fluid from the body is provided. The method includes providing a catheter system which includes an inner lumen, the proximal end of which is connected to an infusion mechanism configured to control infusion of a fluid, and an outer lumen, the proximal end of which is connected to an aspiration mechanism configured to control aspiration of fluid from the body. The method also includes activating the infusion mechanism to infuse fluid into the body for a first infusion time period and at a first infusion pressure, disabling the infusion mechanism to stop infusion, and activating the aspiration mechanism to aspirate fluid for a first aspiration time period and at a first aspiration pressure.

26 Claims, 2 Drawing Sheets

(56) References Cited

U.S. PATENT DOCUMENTS

| | | | |
|---|---|---|---|
| 4,228,802 A | 10/1980 | Trott | |
| 4,694,832 A * | 9/1987 | Ungerstedt | A61B 5/14528 600/366 |
| 4,752,289 A * | 6/1988 | Balding | A61M 5/16854 128/DIG. 13 |
| 4,755,175 A | 7/1988 | Nilsson | |
| 5,213,571 A * | 5/1993 | Fujio | A61M 1/0058 604/22 |
| 5,312,400 A * | 5/1994 | Bales | A61B 17/3203 606/41 |
| 5,562,612 A * | 10/1996 | Fox | A61F 9/00736 604/22 |
| 6,379,326 B1 * | 4/2002 | Cimino | A61M 1/0047 604/30 |
| 2004/0059363 A1 * | 3/2004 | Alvarez | A61B 17/32002 606/170 |
| 2006/0173244 A1 * | 8/2006 | Boulais | A61B 1/00085 600/156 |

FOREIGN PATENT DOCUMENTS

| | | |
|---|---|---|
| WO | 03089031 A1 | 10/2003 |
| WO | 2005023354 | 3/2005 |

* cited by examiner

FLUID EXCHANGE CATHETER SYSTEM

CROSS REFERENCE TO RELATED APPLICATIONS

This application claims priority as a divisional of U.S. patent application Ser. No. 12/065,019, filed on Feb. 27, 2008, which issued as U.S. Pat. No. 8,398,581, which is the national stage of International Application No. PCT/GR2006/000043, filed on Aug. 25, 2006, which claims priority to Greek Patent Application No. 20050100452, filed on Sep. 2, 2005, the contents of each of which are expressly incorporated herein by reference.

BACKGROUND OF THE INVENTION

Field of the Invention

The present invention relates to a catheter's system that can be used for infusion of fluids (drugs, water and nutrients) to the body, with concurrent aspiration of biological material (blood, pus, pathological tissue, toxic substances) from the body, in human and, or, animal tissue, without any blockage problems.

Description of Related Art

There are many kinds of catheters which are used for fluid infusion and aspiration in a clinical or preclinical setting. Traditionally, the catheter's tip that is inserted in biological material, is called "distal" and the tip that stays outside is called "proximal".

Most of existing catheters have a single lumen and through this lumen the user can alternatively infuse or aspirate liquids.

For example, in a clinical setting, the common intravenous catheter either aspirates blood samples—usually immediately after it's insertion to the vein—or infuses solutions of drugs and, or, nutrients—usually for many hours or days following insertion.

These catheters can infuse or aspirate large quantities of liquids, but they cannot do it concurrently in order to have a constant exchange of drugs and nutrients with the extra-cellular fluid or pathological liquid accumulations of the tissue.

The concurrent fluid exchange is desirable both for monitoring and therapeutic reasons.

There are few catheters with multiple lumina, which can concurrently infuse and aspirate liquids.

For example, the microdialysis catheter after its introduction to a human or animal tissue is continuously perfused with liquid solutions from a pump connected to its proximal tip. The catheter consists of two concentric lumina, or tubes, that are covered at their distal tip by a membrane. Usually the central tube is the efferent and the peripheral tube is the afferent part of the catheter. Part of the perfused liquid is infused to the tissue through the catheter's membrane at its distal end, and extra-cellular fluid is aspirated through the same membrane and the efferent lumen.

Microdialysis catheters and similar catheters, however, were designed for tissue monitoring, and the above described concurrent infusion and aspiration takes place at a few microliter/minute rate flow range and through very small membrane pores.

For therapeutic applications we need much greater liquid exchange rate and membranes or cages with big pores so that it is possible to evacuate low viscosity liquids like pus that block all existing catheters.

A common problem of all kinds of existing catheters for biological fluids is their blockage, due to corking of biological material into their lumen's tip or its covering.

For example, the end therapy catheter system claims to possess the desired liquid exchange rate and blockage free operation through a moving part.

It consists of two concentrical tubes, one infusing and one aspirating, connected properly to infusion and aspiration devices at their proximal tip, and having a filter or membrane or grid or mesh cage covering their distal tip, which contains a hydrodynamically moving device for concurrent infusion and aspiration. The infusing tube is appropriately connected to a moving device that irrigates the surrounding the catheter space, while simultaneously propels with its movement the aspiration through the other tube.

The following documents are considered the most relevant state of the art as mentioned above:

D1: U.S. Pat. No. 4,694,832 (UNGERSTEDT CARL U) 22 Sep. 1987;

D2: U.S. Pat. No. 4,755,175A (NILSSON LEIF) 5 Jul. 1988; and

D3: PCT/GR2004/000045, IPC A61M 25/00, (PANOTOPOULOS CHRISTOS), 8 Sep. 2003.

SUMMARY OF THE INVENTION

According to the present invention, provided is a fluid exchange catheter system, including infusion and aspiration devices connected to a catheter having two or more lumina. The system further includes a mechanism for creating programmable changes of pressure in infusing and aspirating lumen of the catheter. Accordingly, infused fluids mix with biological fluids, and the mechanism allows this fluid mixture to evacuate without catheter blockage.

DESCRIPTION OF THE PREFERRED EMBODIMENTS

Figure 1:
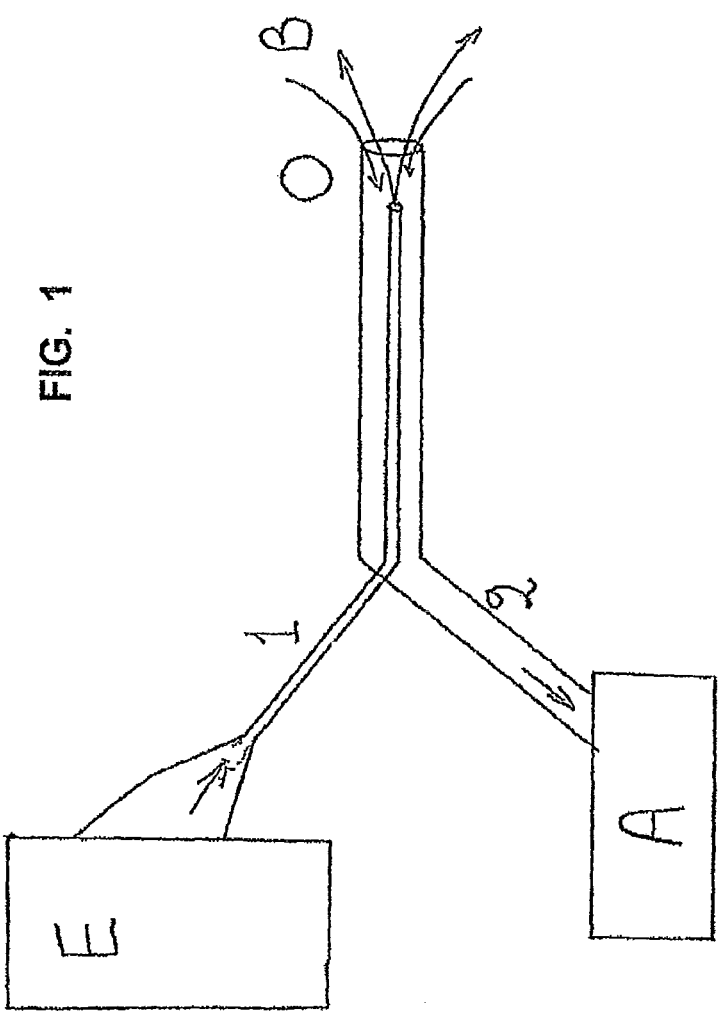
FIG. 1 is a schematic view of one embodiment of a fluid exchange catheter system according to the present invention.
Figure 2:
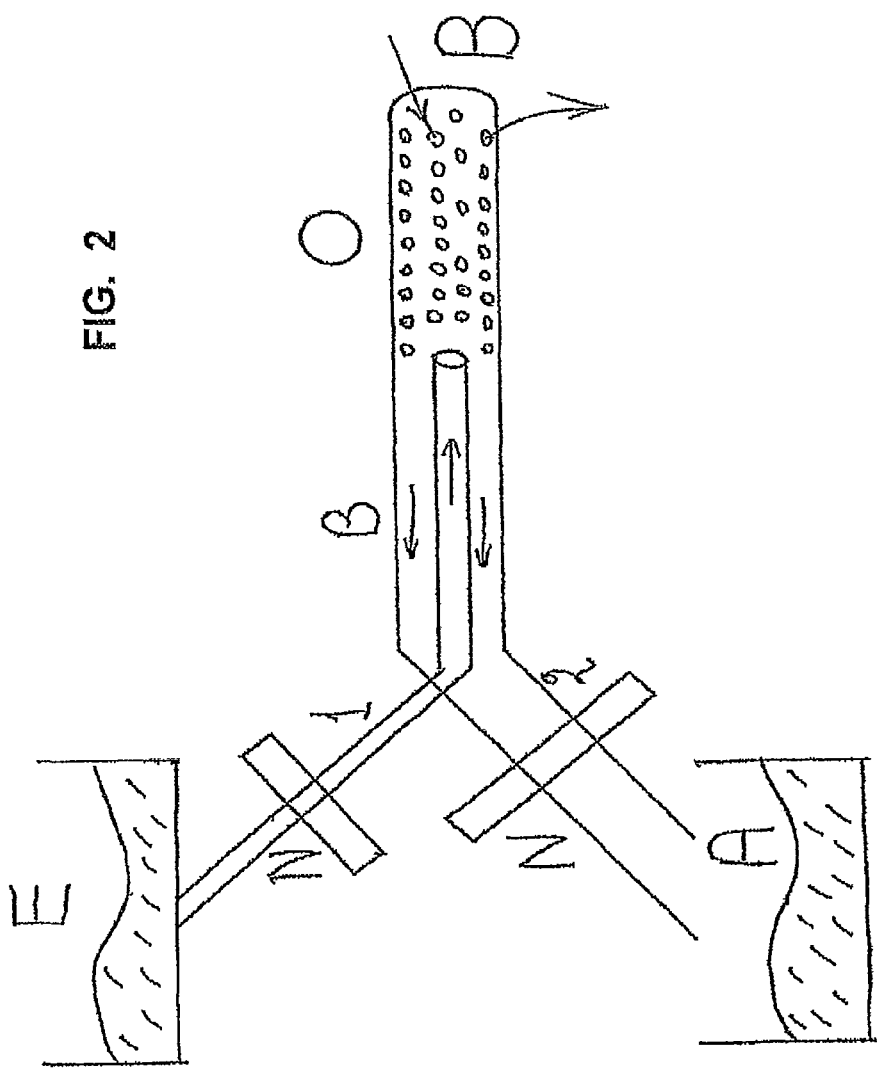
FIG. 2 is a schematic view of another embodiment of a fluid exchange catheter system according to the present invention.

As illustrated in schematic form in FIGS. 1 and 2, provided is a fluid exchange catheter system including two or more lumina, or tubes, (1, 2), connected properly to infusion (E) and aspiration (A) devices at their proximal tips, and having a filter or membrane or grid or mesh cage or no covering over their distal tips (O). These infusion and aspiration devices periodically and, or, continuously change liquid pressure gradients in the system (nevertheless assuring a flow rate that meets the needs for infusion and aspiration of the underlying pathology, or the monitoring, or therapeutic, or research protocol's, needs), in order to create fluid currents (B) that wash clean the catheter's tip and keep unobstructed the fluid exchange between the catheter and the tissue, without the need of any moving parts.

The pressure differences in the system are created by any pattern of positive pressures of the infusing pump and the accordingly synchronized pattern of negative pressures of the aspirating pump (pressures always refer to the pressure at the catheter's tip surrounding tissue).

The system allows a fully and safely controllable infusion-aspiration rate and unobstructed fluid exchange.

For example, in one of the many possible system's versions regarding construction and operational mode, a peristaltic pump (E) is programmed to infuse the liquid with a +200 mmHg pressure for 5 sec followed by 10 sec of stop, while the aspirating tube is blocked (N), and a peristaltic pump (A) is programmed to aspirate with a −100 mmHg pressure during the next 15 sec, while the infusing tube is blocked (N), in a 30 sec cycle of operation.

Lots of patterns of pressure changes can be applied depending on the underlying pathology or the research protocol. Both these (infusion and aspiration) pressures at the ends of the system, can be monitored to be kept synchronized into a predetermined range and phase difference and can be protected by alarms and automatic stops (N), whenever there is any system's dysfunction detection, by flow and, or, pressure detector devices (N) placed appropriately in the system for safety (against over-infusion, over-aspiration etc).

Alternatively the infusion and aspiration devices of the system can be fluid containers (E, A), simply using the hydrostatic pressure forces created by their position relative to the catheter's tip, as moving forces for the infused fluid to enter and the aspirated fluid to leave the tissue at the catheter's insertion site.

For this version of the fluid exchange catheter's system, we could simply include only one automatic button (N) programmed to compress the aspirating (and infusing) tube for 5 sec, followed by 5 sec of free flow of the aspirated (and infused) fluid or programmed for any other pattern of time intervals for free and blocked flow.

Any mode of synchronized changes of pressure at any point of the fluid exchange catheter's system, is transferred directly at the infusing and aspirating tip of the catheter through the liquid column of infused or aspirated fluids.

FIGS. 1 and 2 represent some of the many possible variations of the fluid exchange catheter's system.

The fluid exchange catheter has a bifurcation part of any configuration, in order to split the two opposite flows in two different lumina.

The distal end of the outer lumen-tube holds an exchange surface that can be a filter or membrane or grid or mesh cage or nothing—just the open tip of the aspirating lumen.

Fluid, which can vary from distilled water to nutrient solutions with drugs, that is supplied through the infusion device (E) to the inner lumen-tube (1), reaches the distal end of the catheter (O), where substance exchange occurs between the infused fluid and substances contained in the surrounding tissue's extracellular fluid. The fluid mixture returns to an aspiration device or collection tank (A). Arrows represent pressure gradients.

In order to remove organic substances that are built up on the exchange surface, and consequently block the catheter, a fluid jet, receiving its supply from the inner lumen's hole(s), is dispersed against the liquid exchange surface's inner wall periodically, unblocking thus the membrane or mesh or grid or filter covering. When just the open tip of the aspirating lumen is the exchange surface, the jet from the infusing lumen unblocks the aspirating lumen.

The construction material of the catheter's system should be in conformity to the norms and regulations existing for clinical and laboratory catheters, including bio compatibility issues etc.

The invention claimed is:

1. A method of infusing and aspirating fluid from the body, comprising:
   a) providing a catheter system, comprising:
      i) an inner lumen having a proximal end and a distal end, wherein the proximal end of the inner lumen is connected to an infusion fluid source;
      ii) an infusion mechanism operably connected with the inner lumen;
      iii) an outer lumen having a proximal end, a distal end and a lumen wall extending between the proximal end and the distal end forming an interior lumen space, wherein the distal end of the inner lumen is disposed within the interior lumen space; and
      iv) an aspiration mechanism operably connected with the outer lumen;
   b) activating the infusion mechanism to infuse fluid from the infusion fluid source through the inner lumen and into the body for an infusion time period and at an infusion pressure and infusion flow rate;
   c) disabling the infusion mechanism to stop infusion; and
   d) activating the aspiration mechanism to aspirate fluid from the body through the aspiration lumen for an aspiration time period and at an aspiration pressure and aspiration flow rate,
   wherein the aspiration mechanism is disabled at least during step b) and the infusion mechanism is disabled at least during step d).

2. The method of claim 1, further comprising:
   dispersing a fluid jet from the inner lumen against an exchange surface disposed at the distal end of the outer lumen.

3. The method of claim 1, further comprising:
   e) disabling the aspiration mechanism to stop aspiration.

4. The method of claim 3, further comprising repeating steps b) through e).

5. The method of claim 1, wherein step c) includes disabling the aspiration mechanism and the infusion mechanism to stop aspiration and infusion for a delay period.

6. The method of claim 1, wherein the infusion pressure is a positive pressure and the aspiration pressure is a negative pressure.

7. The method of claim 3, further comprising repeating steps b) through e) to create a pattern of positive pressure in the inner lumen and a synchronized pattern of negative pressure in the outer lumen.

8. The method of claim 1, wherein the infusion time period is less than the aspiration time period.

9. The method of claim 5, wherein the delay period is greater than the infusion time period.

10. The method of claim 1, further comprising monitoring at least one of the infusion pressure and the aspiration pressure.

11. The method of claim 1, further comprising monitoring at least one of the infusion flow rate and the aspiration flow rate.

12. The method of claim 10, further comprising disabling at least one of the infusion mechanism and the aspiration mechanism if the infusion pressure or the aspiration pressure is outside of a predetermined range.

13. The method of claim 11, further comprising disabling at least one of the infusion mechanism and the aspiration mechanism if the infusion flow rate or the aspiration flow rate is outside of a predetermined range.

14. The method of claim 10, further comprising issuing an alarm if the infusion pressure or the aspiration pressure is outside of a predetermined range.

15. The method of claim 11, further comprising issuing an alarm if the infusion flow rate or the aspiration flow rate is outside of a predetermined range.

16. A method of infusing and aspirating fluid from the body, comprising:
a) providing a catheter system, comprising:
i) an inner lumen having a proximal end and a distal end, wherein the proximal end of the inner lumen is connected to an infusion fluid source;
ii) an infusion mechanism operably connected with the inner lumen;
iii) an outer lumen having a proximal end, a distal end and a lumen wall extending between the proximal end and the distal end forming an interior lumen space, wherein the distal end of the inner lumen is disposed within the interior lumen space; and
iv) an aspiration mechanism operably connected with the outer lumen;
b) activating the infusion mechanism to infuse fluid from the infusion fluid source through the inner lumen and into the body for an infusion time period and at an infusion pressure and infusion flow rate while the aspiration mechanism is disabled;
c) disabling the infusion mechanism to stop infusion;
d) activating the aspiration mechanism to aspirate fluid from the body through the aspiration lumen for an aspiration time period and at an aspiration pressure and aspiration flow rate while the infusion mechanism is disabled;
e) disabling the aspiration mechanism to stop aspiration;
f) repeating steps b) through e); and
g) periodically dispersing a fluid jet from the inner lumen against an exchange surface disposed at the distal end of the outer lumen.

17. The method of claim 16, wherein step c) includes disabling the aspiration mechanism and the infusion mechanism to stop aspiration and infusion for a delay period.

18. The method of claim 17, wherein the delay period is longer than the infusion time period.

19. The method of claim 16, further comprising monitoring at least one of the infusion pressure, the infusion flow rate, the aspiration pressure, and the aspiration flow rate.

20. A method of infusing and aspirating fluid from the body, comprising:
a) providing a catheter system, comprising:
i) an inner lumen having a proximal end and a distal end, wherein the proximal end of the inner lumen is connected to an infusion fluid source;
ii) an infusion mechanism operably connected with the inner lumen;
iii) an outer lumen having a proximal end, a distal end and a lumen wall extending between the proximal end and the distal end forming an interior lumen space, wherein the distal end of the inner lumen is disposed within the interior lumen space; and
iv) an aspiration mechanism operably connected with the outer lumen;
b) activating the infusion mechanism to infuse fluid from the infusion fluid source through the inner lumen and into the body for an infusion time period and at an infusion pressure and infusion flow rate while the aspiration mechanism is disabled;
c) disabling the infusion mechanism to stop infusion;
d) activating the aspiration mechanism to aspirate fluid from the body through the aspiration lumen for an aspiration time period and at an aspiration pressure and aspiration flow rate while the infusion mechanism is disabled;
e) disabling the aspiration mechanism to stop aspiration;
f) repeating steps b) through e);
g) periodically dispersing a fluid jet from the inner lumen against an exchange surface disposed at the distal end of the outer lumen;
h) monitoring at least one of the infusion pressure, the infusion flow rate, the aspiration pressure, and the aspiration flow rate; and
i) disabling at least one of the infusion mechanism and the aspiration mechanism if the infusion pressure, infusion flow rate, aspiration pressure, or aspiration flow rate is outside of a predetermined range.

21. The method of claim 1, wherein the method is used to treat an extra-cellular fluid or pathological liquid accumulation in a portion of body tissue.

22. A method of treating an extra-cellular fluid or pathological liquid accumulation in a portion of body tissue using a catheter system, comprising:
a) providing the catheter system, the catheter system comprising:
i) an inner lumen having a proximal end and a distal end;
ii) an infusion mechanism operably connected with the inner lumen;
iii) an outer lumen having a proximal end, a distal end and a lumen wall extending between the proximal end and the distal end forming an interior lumen space, wherein the distal end of the inner lumen is disposed within the interior lumen space; and
iv) an aspiration mechanism operably connected with the outer lumen;
b) positioning the distal end of the inner lumen and the distal end of the outer lumen in fluid communication with the extra-cellular fluid or pathological liquid accumulation;
c) activating the infusion mechanism to infuse an infusion fluid through the inner lumen and into contact with the extra-cellular fluid or pathological liquid accumulation;
d) disabling the infusion mechanism to stop infusion; and
e) activating the aspiration mechanism to aspirate at least a portion of the extra-cellular fluid or pathological liquid accumulation,
wherein the aspiration mechanism is disabled at least during step c) and the infusion mechanism is disabled at least during step e).

23. The method of claim 22, wherein the infusion fluid comprises at least one drug, at least one nutrient, or a combination of at least one drug and at least one nutrient.

24. The method of claim 22, further comprising:
dispersing a fluid jet from the inner lumen against an exchange surface disposed at the distal end of the outer lumen.

25. The method of claim 22, further comprising:
f) disabling the aspiration mechanism to stop aspiration.

26. The method of claim 25, further comprising repeating steps c) through f).

* * * * *